(12) United States Patent
Lu

(10) Patent No.: US 6,464,499 B1
(45) Date of Patent: Oct. 15, 2002

(54) AIR-SUCKING, STERILIZING AND WASTEWATER TREATMENT METHOD FOR DENTAL CLINIC BED

(76) Inventor: Li-Chou Lu, No. 1, Lane 421, Chung Cheng Rd., Hsinchung, Taipei (TW)

(*) Notice: Subject to any disclaimer, the term of this patent is extended or adjusted under 35 U.S.C. 154(b) by 0 days.

(21) Appl. No.: 09/827,237

(22) Filed: Apr. 6, 2001

(51) Int. Cl.[7] .............................................. A61C 17/06
(52) U.S. Cl. ........................... 433/92; 433/29; 433/91; 433/97
(58) Field of Search ............................. 433/91, 92, 96, 433/97, 29

(56) References Cited

U.S. PATENT DOCUMENTS

| | | | | |
|---|---|---|---|---|
| 2,895,220 A | * | 7/1959 | Johnston et al. ............... | 433/92 |
| 3,138,873 A | * | 6/1964 | Bishop ........................ | 433/92 |
| 3,226,733 A | * | 1/1966 | Ashton ........................ | 433/96 |
| 3,537,447 A | * | 11/1970 | Gauthier et al. ............... | 433/29 |
| 3,665,682 A | * | 5/1972 | Ciavattoni et al. ............. | 433/92 |
| 3,988,134 A | * | 10/1976 | Gandrud ....................... | 433/92 |
| 4,446,861 A | * | 5/1984 | Tada .......................... | 128/863 |
| 5,354,468 A | * | 10/1994 | Richards ...................... | 433/92 |
| 5,547,375 A | * | 8/1996 | Schneider ..................... | 433/96 |
| 5,636,627 A | * | 6/1997 | Rochester ..................... | 433/25 |
| 5,885,076 A | * | 3/1999 | Ralls et al. .................. | 433/92 |
| 5,925,257 A | * | 7/1999 | Albelda et al. ................ | 433/80 |
| 5,931,670 A | * | 8/1999 | Davis ......................... | 433/91 |

* cited by examiner

*Primary Examiner*—John J. Wilson

(57) ABSTRACT

This is an air-sucking, sterilizing and wastewater treatment method for dental clinic bed. It has an air-sucking and sterilizing device, and a wastewater-treating device below a gargle bench of a dental clinic bed. The air-sucking inlet of the air-sucking and sterilizing device is connected above the bench top to an air-sucking pipe that can be bent to form. At the other end of the air-sucking pipe is an air-sucking mask equipped with a clinical lamp. Utilizing the bendable property of the air-sucking pipe, the dentist can adjust the air-sucking mask with the clinical lamp to an optimum position, to collect germ-carrying flying saliva and volatile chemicals produced in the clinical process, or the flying moisture from the tooth grinding machine in the air-sucking and sterilizing device. Inside the air-exhaust valve is a ion device for purifying purpose to enhance hygienic quality of the entire clinical process, and avoid unnecessary contamination of flying saliva. The wastewater-treating device will clean the patient's mouth and chemical solutions and germ-carrying wastewater, filter and sterilize it thoroughly before discharging it, so the discharged wastewater will not pollute river sources.

4 Claims, 4 Drawing Sheets

AIR-SUCKING, STERILIZING AND WASTEWATER TREATMENT METHOD FOR DENTAL CLINIC BED

BACKGROUND OF THE INVENTION

1. Field of The Invention

The present invention relates to a cleaning system for foul fluid in a dental clinic bed, and, particularly, to a cleaning system, in which a aspirating device and a wastewater treatment device are provided under a dental clinic bed to aspirate, sterilize, deodorize and purify the foul fluid such as the flying saliva, the flying moisture, the volatile chemical solution and the germ-carried wastewater, such that the hygienic quality can be enhanced and the unnecessary contamination or cross infection can be avoided effectively in the process of dental clinic treatment.

2. Description of Related Art

Conventionally, a patient has to open his mouth wide for the dentist to conduct an oral examination and a medical treatment during the process of dental clinic treatment. However, the dentist could easily be infected because of the germ-carried flying saliva of the patient and the mouth odor of the patient could affect the dentist's medical quality. In addition, the therapeutic room may be filled with a large amount of germs in company with bad smell such that it becomes a sound place for cross infection. Furthermore, when the dentist conducts a grinding job for the teeth in the patient's mouth, a large amount of moisture may come out of the tooth grinding machine to spread around the oral cavity of the patient such that the spread moisture may stains on faces or clothing of the patient himself, the dentist and the medical assistances aside to cause them discomfort. Moreover, the flying moisture could contain the tooth debris, the blood, the volatile chemical solution and the germ carried saliva so that the entire therapeutic room are contaminated and it can result in a much greater chance of cross infection.

SUMMARY OF THE INVENTION

The crux of a cleaning system for foul fluid in a dental clinic bed according to the present invention resides in that an aspirating device and a wastewater treatment device are installed beneath a garble bench of the dental clinic bed and an aspirating mask with a clinical lamp is disposed over the dental clinic bed to communicate with the aspirating device by way of a bendable pipe. The aspirating musk can be located at an optimum position due to the bendable property thereof so that the aspirating device can aspirate, sterilize and deodorize the flying saliva, the volatile chemical solution and the flying moisture during the dental clinic treatment being performed and the wastewater treatment device can collect, treat and purify the water from the aspirating device and the wastewater from the gargle bench.

Accordingly, an objective of the present invention is to provide a cleaning system for foul fluid in a dental clinic bed for the hygienic quality of the dental clinic treatment is capable of being enhanced substantially and any unnecessary contamination and cross infection can be avoided effectively.

Another objective of the present invention is to provide a cleaning system for foul fluid in a dental clinic bed in which a disposable inner musk is attached to the sucking mask and the inner musk can be renewed regularly to satisfy the need of personal hygiene.

BRIEF DESCRIPTION OF THE DRAWINGS

The detail structure, the applied principle, the function and the effectiveness of the present invention can be more fully understood by reference to the following description and accompanying drawings, in which.

DETAILED DESCRIPTION OF THE PREFERRED EMBODIMENT

Figure 1:
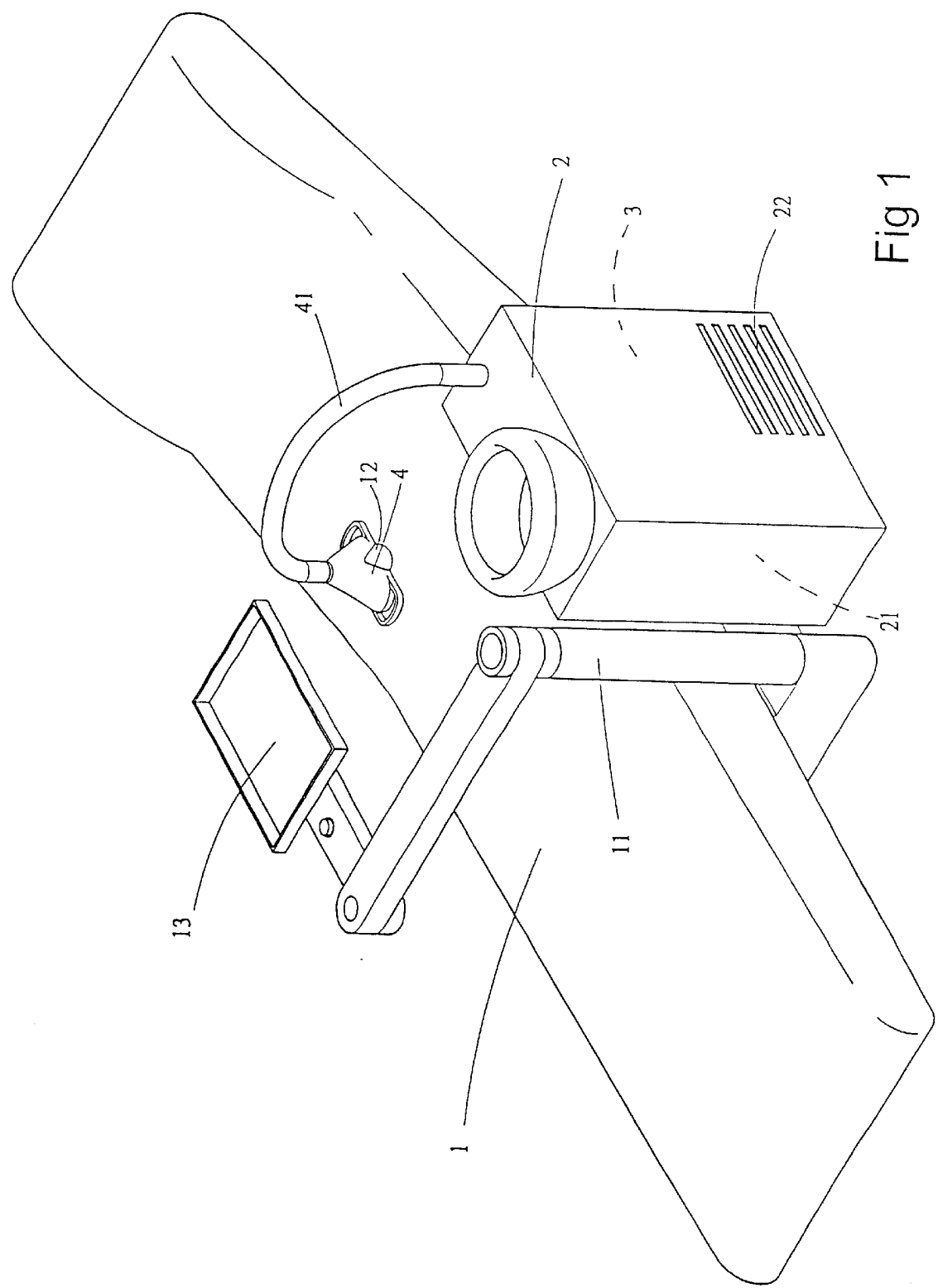
FIG. 1 is a perspective view of a dental clinic bed associated with a cleaning system for foul fluid according to the present invention in a preferred embodiment thereof.
Figure 2:
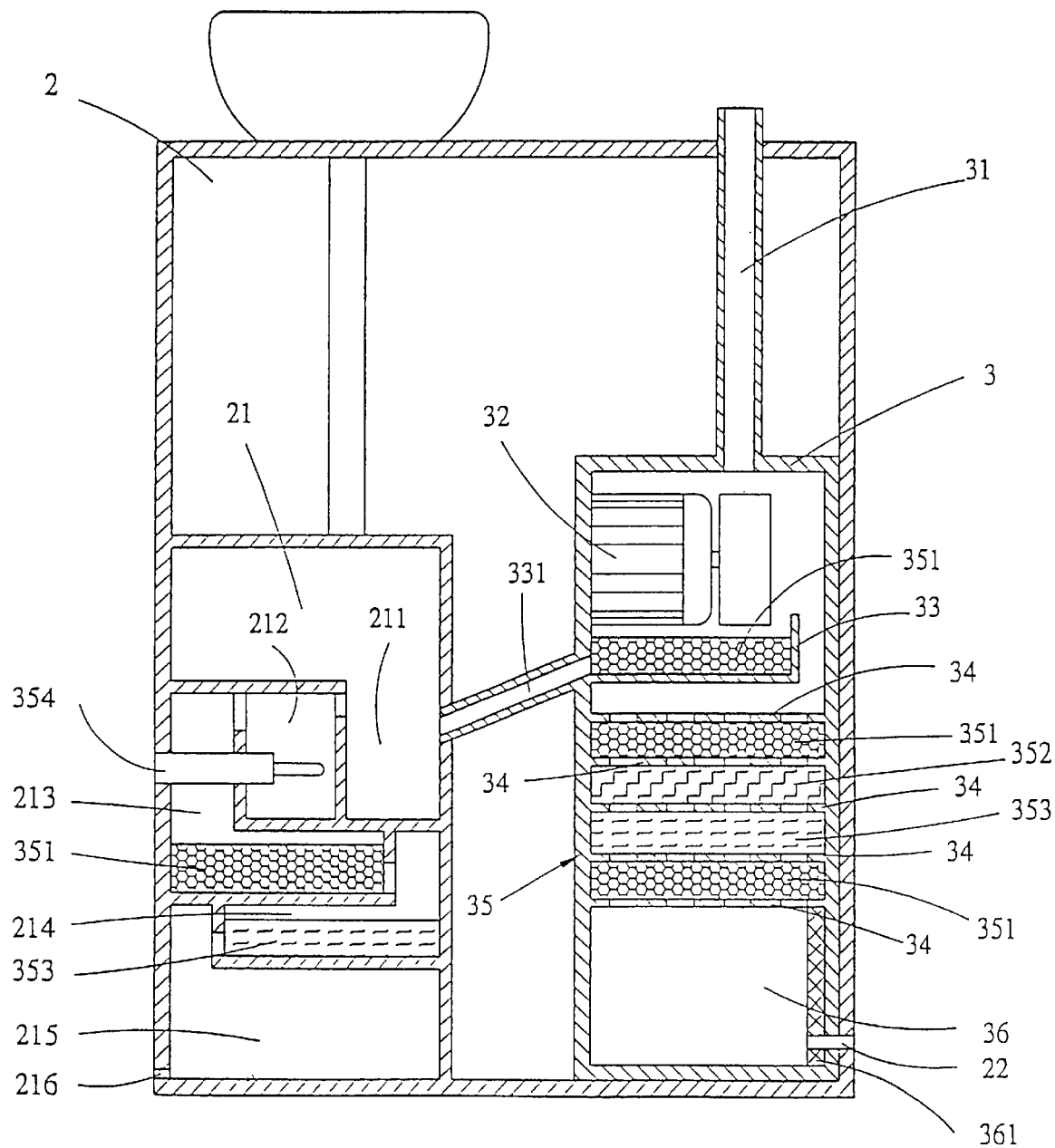
FIG. 2 is a sectional view illustrating a aspirating device and a wastewater treatment device in the cleaning system for foul fluid of the present invention in the preferred embodiment shown in FIG. 1.
Figure 3:
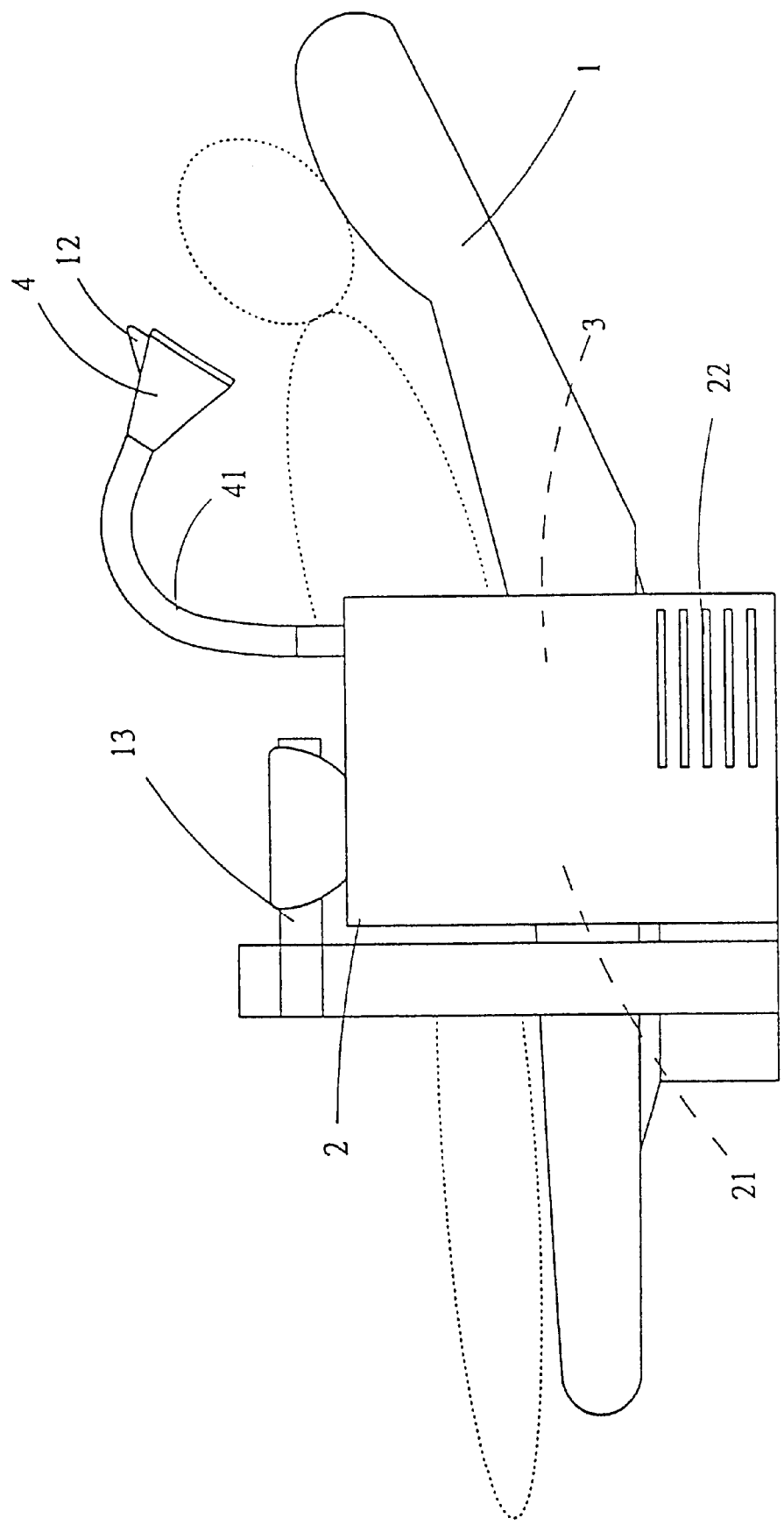
FIG. 3 is a plan view of a lateral side of dental clinic bed shown in FIG. 1 illustrating how the cleaning system for foul fluid of the present invention is used.

Referring to FIGS. 1 and 2, a cleaning system for foul fluid in a dental clinic bed according to the present invention comprises a bed unit 1, an aspirating device 3, a wastewater treatment device 21 and an aspirating musk 4. The bed unit 1 further comprises a gargle bench 2, a support arm 11 and a working plate 13. The support arm 13 is disposed beside the gargle bench 2 and the working plate 13 is attached to an end of the support arm 11. The aspirating device 3 and the wastewater treatment device 21 are arranged beneath the gargle bench 2 and the aspirating device is disposed next to the wastewater treatment device 21. The aspirating musk 4 is disposed over the bed unit 1 and a bendable pipe 41 is provided to have an end thereof being joined to the aspirating musk 4. The bendable pipe 4 at another end thereof is connected to an inlet pipe 31 of the aspirating device 3. The aspirating musk 4 can be adjustably located at an optimum position by way of the bendable property of the bendable pipe 41 such that the flying saliva and the volatile chemical solution resulting from the dental clinic treatment and the flying moisture coming out of the tooth grinding machine can be sucked into the aspirating device for being treated with further processing as soon as a sucking motor 32 at the upper level of the aspirating device starts to run.

Referring to FIG. 2 again, the aspirating device further includes a filtering structure 35 and at least a filtering cotton layer 351, a sterilizing layer 352 and an active carbon layer 353 are arranged in the filtering structure 35 to space apart from each other by way of a grid plate partition 34 respectively. Hence, the flying saliva, the volatile chemical solution and the flying moisture aspirated in the aspirating device 3 can be filtered, sterilized and deodorized sequentially such that the discharged air from the filtering structure 35 enters a discharge chamber 36 underneath the filtering structure 35 and is purified by a negative ion device 361 in the discharged chamber 36 before the discharged air can be released through an air output port 22. Further, the inlet pipe 31 is disposed at the top of the aspirating device to extend upward so as to connect with the other end of preceding bendable pipe 41. A water collecting plate 33 is disposed above the filtering structure 35 in the aspirating device 3 to collect the water coming from the aspirating musk 4 and is lined with a further filtering cotton layer to avoid foreign substances entering a water drain pipe 331 disposed between the aspirating device and the wastewater treatment device 21 with an end thereof being connected to the bottom of the water collecting plate 33 and the other end thereof being connected to an upper lever of the wastewater treatment device. Besides, the upper lever of the wastewater treatment device 21 is partitioned into a water collection chamber 211 and a sterilizing chamber 212, wherein, the water collection chamber 211 can collect the wastewater coming from the gargle bench 2 and the water collecting plate 33 and the collected wastewater then can flows to the sterilizing chamber 212. A sterilizing device 354 is arranged in the sterilizing chamber 212 to sterilize the wastewater therein. After being treated by the sterilizing device 354, the sterilized wastewater flows into a filtering chamber 213 and a deodorizing chamber 214 at a lower level of the wastewater treatment device 21 from a lateral side of the sterilizing device 354 such that the sterilized wastewater can be treated with a further filtering cotton layer 351 in the filtering chamber 213 and another active carbon layer 353 in the deodorizing chamber 214. Finally, the purified wastewater flows into a pure water chamber 215 at the bottom of the wastewater treatment device 21 before it can flow out via a water output port 216.

Figure 4:
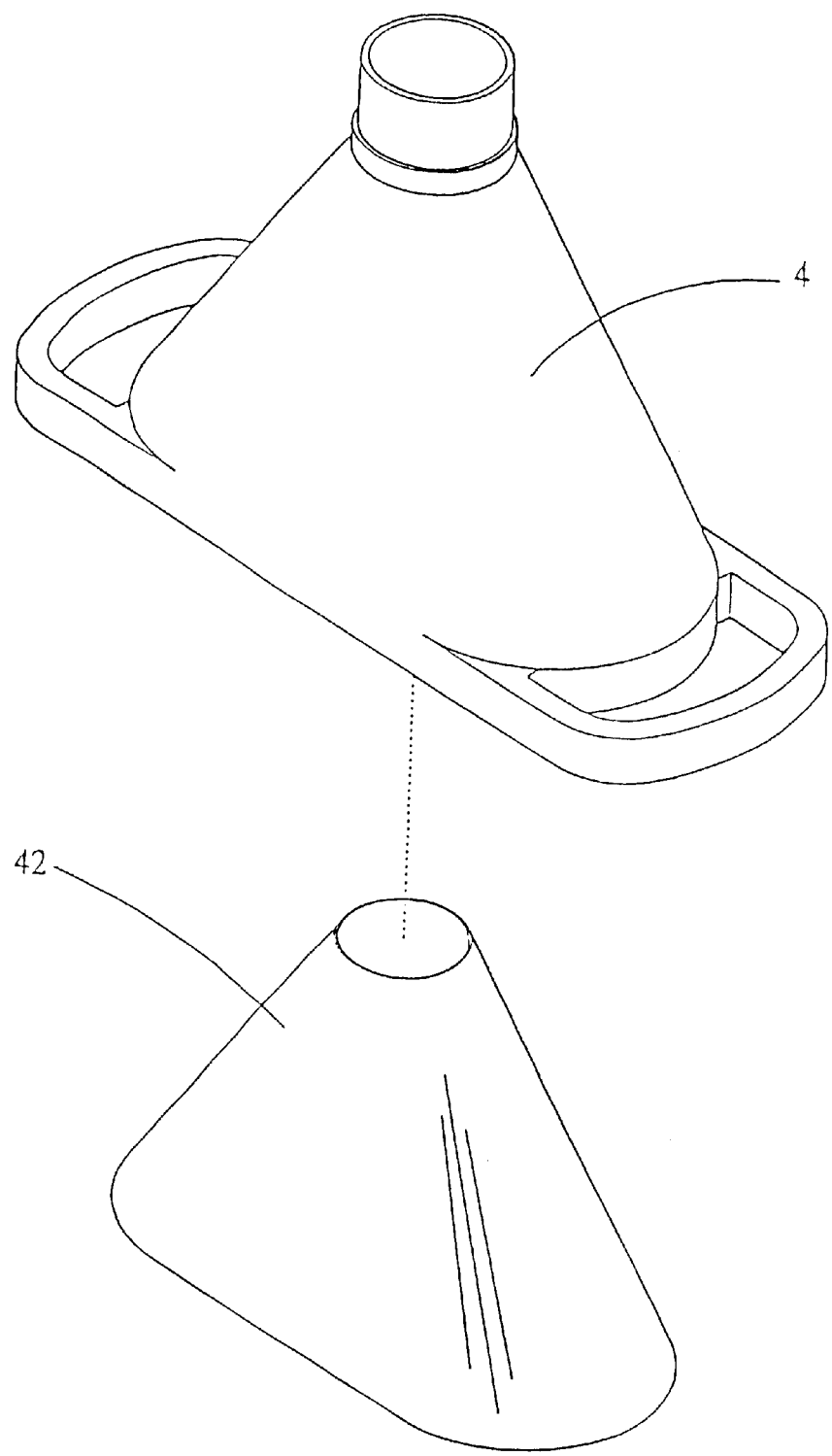
FIG. 4 is a disassembled perspective view of a aspirating musk with a detached disposable inner musk.

Referring to FIG. 4, the aspirating mask 4 at the inside thereof is attached with a disposable inner musk 42 so that the inner musk 42 can be renewed regularly to prevent the sucking mask 4 from being contaminated by the flying saliva and can satisfy the need of personal hygiene. In addition, the aspirating musk 4 is associated with a clinical lamp 12 as an integral unit as shown in FIG. 1 so that it is possible to save the space available for the clinical lamp 12 and the aspirating musk 4 with the clinical lamp 12 can be adjustably located at any position nearest to each patient individual conveniently in the process of dental treatment.

It is appreciated from the preceding description of the preferred embodiment that the cleaning system for foul fluid in a dental clinic bed according to the present invention provides an aspirating device and a wastewater treatment device beneath a gargle bench of the dental clinic bed to aspire, filter, sterilize and deodorize the foul fluid such as the flying saliva and the volatile chemical solution during the dental clinic treatment and the flying moisture coming out of the tooth grinding machine effectively. Further, an aspirating musk attached with a disposable inner musk is connected to the aspirating device with a bendable pipe such that the aspirating musk can be moved and located at a position nearest to the patient's mouth to collect the foul fluid as much as possible. Hence, the hygienic quality of the dental clinic treatment can be enhanced substantially and the unnecessary contamination or cross infection can be avoided advantageously. Moreover, the inner musk can be renewed regularly so as to satisfy the need of personal hygiene.

While the invention has been described with referencing to a preferred embodiment thereof, it is to be understood that modifications or variations may be easily made without departing from the spirit of this invention, which is defined by the appended claims.

What is claimed is:

1. A cleaning system for foul fluid in a dental clinic bed, comprising:
   a bed unit, providing a gargle bench and a support arm with a working plate at one side thereof;
   an aspirating device, being disposed under the gargle bench, having an inlet pipe at a top surface thereof extending upward through the gargle bench;
   a wastewater treatment device, being disposed under the gargle bench beside the aspirating device and connected to the aspirating device with a drainpipe, and a top surface thereof communicating with the gargle bench; and
   an aspirating musk, being associated with a clinical lamp, being disposed over the bed unit and connected to the inlet pipe of the aspirating device by way of a bendable pipe with an end of the bendable pipe being joined to the aspirating musk and the other end thereof to the inlet pipe respectively;

wherein, the aspirating device further comprises:
   a water connecting plate, being disposed at an upper level of the aspirating device, being lined with a layer of filtering cotton at an bottom thereof, and being at the bottom communicating with the drainpipe; and
   a filtering structure, being under the water connecting plate, providing at least a filtering cotton layer, a sterilizing layer and an active carbon layer being arranged sequentially with any two neighboring layers being spaced apart by a grid plate respectively; and
   whereby, the aspirating musk with the clinical lamp can be located at an optimum position by a dentist adjusting the bendable pipe and the foul fluid such as flying saliva, volatile chemical solution produced in a process of dental clinic treatment and flying moisture from a tooth grinding machine can be sucked into the filtering structure of the aspirating device via the sucking musk, the inlet pipe and the water collecting plate so that the foul fluid can be filtered, sterilized and deodorized sequentially and the wastewater from the gargle bench and the water from the drain pipe connected to the water collecting plate can flow into the wastewater treatment device for further treatment so as to enhance hygienic quality in the process of the dental clinic treatment.

2. The cleaning system for foul fluid in a dental clinic bed as defined in claim 1, wherein a sucking motor is arranged at the upper level of the aspirating device to provide a suction force for the aspirating device and a discharge chamber is disposed under the filtering structure with a negative ion device being therein and an air output port at a lateral side thereof for purifying air from the filtering structure before the air being released through the air output port.

3. The cleaning system for foul fluid in a dental clinic bed as defined in claim 2, wherein the aspirating musk is attached with a disposable inner mask tightly due to the suction force such that the aspirating musk can be insulated from the foul fluid; and the inner musk can be renewed regularly to satisfy the need of personal hygiene.

4. The cleaning system for foul fluid in a dental clinic bed as defined in claim 1, wherein the wastewater treatment device further comprises
   a water collection chamber, being disposed at an upper level of the wastewater treatment device to communicate with the drainpipe and the gargle bench;
   a sterilizing chamber, being disposed at the upper level next to and communicating with the water collection chamber, and having a sterilizing device;
   a filtering chamber, being disposed at a lower lever of the wastewater treatment device, communicating with the sterilizing chamber, and providing a further layer of filtering cotton;
   a deodorizing chamber, being disposed at a lower level of the wastewater treatment device and communicating with the filtering chamber, and providing a further layer of active carbon; and
   a pure water chamber, being disposed at a bottom of the wastewater treatment device, communicating with the deodorizing chamber, and providing a water output port at a lateral side thereof;
   whereby, the wastewater from the gargle bench and the water received in the water collecting plate can be sterilized, filtered and deodorized sequentially before flowing out via the water output port.

* * * * *